United States Patent [19]

Molina

[11] 4,152,592

[45] May 1, 1979

[54] WATER WASHABLE DYE PENETRANT COMPOSITION AND METHOD FOR UTILIZING SAME

[75] Inventor: Orlando G. Molina, Westminster, Calif.

[73] Assignee: Rockwell International Corporation, El Segundo, Calif.

[21] Appl. No.: 596,343

[22] Filed: Jul. 16, 1975

Related U.S. Application Data

[63] Continuation-in-part of Ser. No. 444,433, Feb. 21, 1974, Pat. No. 3,915,886.

[51] Int. Cl.² ............................................. G09K 3/00
[52] U.S. Cl. .......................... 250/302; 252/DIG. 1; 252/DIG. 6
[58] Field of Search ........................................ 250/302

[56] References Cited

U.S. PATENT DOCUMENTS

| | | | |
|---|---|---|---|
| 3,118,060 | 1/1964 | Klein | 250/302 |
| 3,349,041 | 10/1967 | Alburger | 252/301.19 |
| 3,429,826 | 2/1969 | Alburger | 252/301.19 |
| 3,543,570 | 12/1970 | Mlot-Fijalkowski | 250/302 |
| 3,558,882 | 1/1971 | Mlot-Fijalkowski | 250/302 |
| 3,716,492 | 2/1973 | Graham et al. | 250/302 |
| 3,915,886 | 10/1975 | Molina | 252/301.19 |
| 3,939,092 | 2/1976 | Molina | 252/301.19 |

*Primary Examiner*—Harold A. Dixon
*Attorney, Agent, or Firm*—Charles T. Silberberg; L. Lee Humphries

[57] ABSTRACT

A water washable substantially biodegradable dye penetrant composition having excellent sensitivity and high stability, for use in non-destructive testing of objects to locate voids and defects therein, said composition consisting essentially of an organic dye, preferably a fluorescent dye, and a carrier or solvent for said dye, in the form of certain ethoxylated linear alcohols, particularly the biodegradable nonionic surfactants comprised of ethoxylates of a mixture of secondary alcohols having linear alkyl chains of from 10 to 17 carbon atoms. In the method of application of the dye penetrant compositions, such composition is applied to the surface of an object containing cracks and flaws, water is applied to the surface of the object to remove excess liquid dye penetrant composition from the surface without removing such penetrant from the cracks and defects, and with or without a developer, the surface of the object is viewed under suitable lighting conditions, e.g., ultraviolet or black light when the dye in the penetrant is a fluorescent dye, to locate any cracks or defects in the surface of the body as indicated by colored traces from the dye penetrant remaining in the cracks and flaws.

18 Claims, No Drawings

WATER WASHABLE DYE PENETRANT COMPOSITION AND METHOD FOR UTILIZING SAME

This application is a continuation-in-part of my co-pending application Ser. No. 444,433, filed Feb. 21, 1974 now U.S. Pat. No. 3,915,886.

BACKGROUND OF THE INVENTION

This invention relates to an improved dye penetrant composition and method for non-destructively testing material specimens to locate and identify surface voids, cracks or defects, and more particularly to an improved liquid vehicle for such a dye penetrant. The inventin is especially concerned with a novel easily water washable, stable and sensitive dye penetrant composition of the above type employing as solvent or vehicle essentially a biodegradable nonionic surfactant in the form of mixtures of certain ethoxylated alcohols; and to a method utilizing such dye penetrant composition for non-destructive testing of parts.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, and methyl ethyl ketone, all highly volatile solvents, have heretofore been employed in prior art dye penetrants. See for example U.S. Pat. No. 2,806,959. Further, most dye penetrant solutions in practice generally require the use of a combination of solvents, including primary and secondary solvents, extender solvents and wetting agents.

However, the use of volatile solvents in dye penetrant compositions has certain disadvantages. Thus, the use of volatile solvents in dye penetrants results in the evolution of fumes and solvent vapors which are rapidly formed by the evaporating solvent.

In addition, stability of the penetrant solution is essential without the necessity for carefully balancing the various liquid components of a dye penetrant solution in order to obtain efficient penetration of the solution into the cracks and flaws of a part, dye solubility, wetting action and washability control.

An additional criterion has recently developed also with respect to dye penetrant solutions and compositions. Generally, dye penetrant solutions presently being used and containing solvents and wetting agents present a disposal problem and hence the necessity for the development of dye penetrant solutions and compositions which are biodegradable, that is which employ dye solvents and carriers which are biodegradable, and are readily available despite the petrochemical shortage, has attained considerable importance.

Accordingly, an object of the present invention is the provision of a readily water washable dye penetrant solution or composition which avoids the use of the conventional volatile solvents and wetting agents and their above-noted disadvantages, and which is highly stable, has excellent sensitivity and is essentially non-flammable and non-toxic. A particular object of the invention is to provide a dye penetrant solution of the above-noted type, having good wettability characteristics, and which employs a single liquid carrier which is readily available and is biodegradable, thus rendering the dye penetrant solution essentially biodegradable.

DESCRIPTION OF THE INVENTION

The above objects and advantages are accomplished according to the invention by providing a dye penetrant composition containing a dye, e.g. a fluorescent dye, in a solvent or carrier for such dye, which is a biodegradable nonionic surfactant in the form of certain ethoxylated alcohols, and particularly the biodegradable surfactants comprised of nonionic ethoxylates of certain isomeric linear alcohols, as described in greater detail hereinafter. This unique dye penetrant composition provides a single or "one liquid" dye penetrant solution, in that it does not require the presence of any additional solvents or wetting agents, generally employed in prior art dye penetrant solutions and compositions. The dye penetrant solution of the invention is accordingly very simple to mix, and to use, is economical, and not only is biodegradable, but the above-noted nonionic solvent carrier for the dye is readily available since it is less dependent on petrochemical sources for its manufacture.

Thus, it has been found according to the present invention that the simple addition of a small amount of dye, preferably in proportions hereinafter disclosed, to the above-noted nonionic ethoxylated alcohols results in an efficient powerful dye penetrant with highly unique and desirable characteristics including instant washability from the surface of parts without loss of dye penetrant solution entrapped within the defects and cracks. Such dye penetrant solution penetrates the cracks and flaws in the surface of parts instantly and without having to wait for relatively long periods for this purpose as in the case of many commercial penetrants. Thus, the invention provides a dye penetrant solution employing a single carrier or vehicle for the dye, while at the same time obtaining high stability of the dye in the carrier, and also obtaining excellent wettability and instant washability of the dye penetrant solution from the part surface without dislodging the dye penetrant from the cracks and flaws in a part surface. Since the above-noted nonionic dye solvent or carrier employed has extremely low volatility it provides uniform and stable dye sensitivity. Further, the nonionic solvent or carrier of the dye penetrant solution hereof has a high flash point and is essentially non-flammable, is substantially odorless, and of particular significance, it is biodegradable.

The nonionic biodegradable solvent or carrier for the dye according to the invention consists of ethoxylates of a mixture of linear secondary aliphatic alcohols, with the hydroxyl groups randomly distributed, the linear aliphatic hydrophobic portion of such alcohols being a mixture of alkyl chains containing in the range from 10–17 carbon atoms, preferably in the range from 11 to 15 carbon atoms, and containing an average of from 3 to 12 moles of ethylene oxide.

The above nonionic biodegradable surfactant employed as carrier for the dye penetrant of the invention is a mixture of compounds which can be represented by the formula:

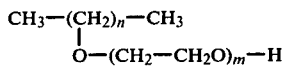

where n is in the range 9 to 13, and m is 3 to 12.

Although preferably each of the immediately above-defined surfactants is formed of a mixture of two or more linear alkyl hydrophobic chains ranging from $C_{11}$ to $C_{15}$ as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary udecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group in the above structural formula. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| Tergitol | 15-S-3 |
| Tergitol | 15-S-5 |
| Tergitol | 15-S-7 |
| Tergitol | 15-S-9 |
| Tergitol | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3.

The nonionic biodegradable surfactants employed as carrier or vehicle for the dye of the penetrant solution according to the invention, are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Any suitable dye generally employed in dye penetrant compositions can be incorporated into the nonionic ethoxylated alcohol surfactants described above for producing the dye penetrant compositions of the invention. Preferably, however, a fluorescent dye is employed for this purpose. The ethoxylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7GA as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g. zyleneazobeta-naphthol, Mefford No. 322 dye, believed to be o-toluene-azoxyleneazo-beta-naphthol, and the azo dyes marketed as Oil Red "0" and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The dye penetrant composition according to the present invention permits rapid and almost instantaneous removal or cleaning of the remaining dye penetrant from the object surface by water washing, e.g. by application of a water spray or a sprayed mixture of air and water, or by wiping with a water moistened cloth or a cloth moistened with a rapid drying solvent such as trichloroethane, without any need for emulsifiers and the like. Thus, the dye penetrant composition hereof generally has excellent wettability and practically instantaneous washability with water without removing dye penetrant from the cracks and defects of the part surface.

However, if desired, small amounts of extenders such as kerosene, and volatile solvents such as methyl ethyl ketone, isopropyl alcohol, and the like, and water, can be added to the dye penetrant composition of the invention containing the ethoxylated alcohol carrier, to vary the properties thereof. It is noted however that in preferred practice these additives are not employed and in effect a "one liquid" solution is provided according to the invention, in which the ethoxylated alcohol surfactant is essentially the sole carrier for the dye. Also, if desired, corrosion inhibitors such as, for example, morpholine, can be added in a small amount such as 0.01 to 0.1% by volume of the dye penetrant composition, particularly where the object being tested is highly susceptible to corrosion, such as magnesium.

The amount of dye which is incorporated into the ethoxylated alcohol surfactant or carrier to produce the dye penetrant composition of the invention, can range from about 0.1 to 15, preferably about 0.5 to about 10, parts of the dye, or mixtures thereof, per 100 parts of the ethoxylated alcohol surfactant, by weight. In preparing the dye penetrant composition of the invention, the dye is simply added to the ethoxylated alcohol carrier, in the desired proportion. The resulting dye penetrant composition has both high and low temperature stability, the stability thereof being such that a test conducted by placing a dye penetrant solution represented by Composition II below, in a hot-air oven at 200° F. for 18 hours did not reduce its performance and it had substantially less loss of solids by evaporation than a standard prior art penetrant solution subjected to the same test.

Where a developer composition is employed, any one of the three general types of developer compositions, namely, dry powder, wet aqueous (water-base) and wet non-aqueous (volatile solvent base) developer compositions can be employed. In each case, the developer composition contains a light colored powder, forming a coating which contrasts with the color of the dye in the penetrant and which acts as a wick or blotter, and causes liquid penetrant containing the dye, e.g. flurescent dye, which was retained in the cracks or surface flaws, to be drawn up out of the surface defects by capillary action and to "bleed" through the powder. Preferred developer compositions for use in conjunction with the dye penetrant composition according to the invention, are those described in my copending application Ser. No. 212,799, filed Dec. 27, 1971, which is a dry powder developer containing fumed alumina, fumed silica, fumed titanium dioxide and talc, and in my U.S. Pat. No. 3,748,469, and which is a wet nonaqueous developer composition consisting essentially of isopropyl alcohol, talc and glycol monobutyl ether. The descriptions of such developer compositions contained in the above copending application and the above patent are incorporated herein by reference.

The dye penetrant composition of the invention employing the above biodegradable nonionic ethoxylated alcohol surfactant can be tailored to have varying degrees of sensitivity for detection of the smallest microcracks to gross cracks in a part surface by generally varying the amount of dye incorporated, and also be selecting particular surfactants or combinations thereof. This is illustrated by the compositions I, II, III and IV in Table 1 below:

TABLE 1

| COMPONENTS | COMPOSITIONS (parts by weight) | | | |
|---|---|---|---|---|
| | I | II | III | IV |
| | Sensitivity Level | | | |
| | Super high | High | Medium | Low |
| Tergitol 15-S-5 | 50.0 | 100.0 | 100.0 | 100.0 |
| Tergitol 15-S-3 | 50.0 | — | — | — |
| Calcofluor White RW | 5.0 | 5.0 | 2.5 | 1.250 |
| Fluorol 7GA | 1.5 | 1.5 | 0.75 | .375 |
| TOTAL | 106.5 | 106.5 | 103.25 | 101.625 |

Composition I, the super high sensitivity dye penetrant material, requires a more rigorous water wash than the high sensitivity material, Composition II, due to the presence therein of Tergitol 15-S-3, which is substantially water insoluble, but provides a very high sensitivity performance. Composition I is particularly advantageous for inspection of parts having a very smooth surface with microcracks. The high sensitivity dye penetrant Composition II is also suitable for this purpose, although not quite as good as Composition I. The medium sensitivity Composition III is suitable for detection of cracks of intermediate size, and low sensitivity dye penetrant Composition IV is employed for detection of gross cracks. It will be noted that the sensitivity of Compositions II to IV varies with the amount of dye present, the sensitivity generally increasing with increase in dye concentration.

All of the above dye penetrant Compositions II, III and IV containing Tergitol 15-S-5 surfactant, and ranging from high to low sensitivity, have essentially the same water washability when subjected to normal washing conditions using a water spray or a water-air spray. These formulations can tolerate addition of substantial amounts of water up to about 16% by volume, without reducing the concentration of dye in the dye penetrant remaining in the cracks and flaws following water washing, and hence without loss in sensitivity.

However, when the amount of water used for washing excess dye penetrant from the surface of a part is materially reduced, it is noted that the amount of dye present in the dye penetrant then controls the water washability characteristics of the formulation. Thus, formulations having the larger amount of dye such as Composition II above are less readily washable than Compositions III and IV, and Composition III is less washable than Composition IV. This is an additional feature of the invention employing the above nonionic ethoxylated alcohol surfactant as carrier for the dye in the dye penetrant, since it permits varying the water washability of the dye penetrant by variation of the amount of a solid, namely the dye, present in the dye penetrant composition.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility in dye penetrants according to the invention when employed in combination with the other water washable Tergitols such as Tergitol 15-S-5 and Tergitol 15-S-9. Representative examples of effective dye penetrant formulations provided by employing a combination of Tergitol 15-S-3 and Tergitol 15-S-9, in varying volumetric proportions, are set forth in Table 2 below. In Table 2, the proportions of Tergitol 15-S-3 and Tergitol 15-S-9 are expressed in terms of volumetric proportions with respect to each other, and the proportions of dye set forth are expressed in terms of percent by weight of the overall composition.

TABLE 2

| | COMPOSITIONS | | |
|---|---|---|---|
| | V | VI | VII |
| | Sensitivity Level | | |
| COMPONENTS | High | Medium | Low |
| Tergitol 15-S-3 | 75 | 50 | 25 |
| Tergitol 15-S-9 | 25 | 50 | 75 |
| Calcofluor White RW | 5.0 | 5.0 | 5.0 |
| Fluorol 7GA | 1.5 | 1.5 | 1.5 |

From Table 2 above, it is seen that the sensitivity of the respective formulations is increased by increasing the amount of Tergitol 15-S-3 employed in the respective formulations in combination with Tergitol 15-S-9. It has been found that combinations of the nonionic biodegradable surfactants, such as combinations of the Tergitols noted above, as represented by Compositions I, V, VI and VII of Tables 1 and 2 above, provide highly satisfactory dye penetrant compositions according to the invention.

Of the various surfactants described above, it has been found that for high sensitivity formulations, dye penetrants containing Tergitol 15-S-5 as the dye carrier provides the optimum, with dye penetrants containing Tergitol 15-S-9 as carrier also being highly effective. Dye penetrants containing Tergitol 15-S-7 as dye carrier or solvent, while effective, are not quite as good as dye penetrants containing Tergitol 15-S-5 or Tergitol 15-S-9. Tergitol 15-S-12 also is effective in the dye penetrant composition of the invention, although again not as effective as the use of the above-noted Tergitols 15-S-5 and 15-S-9. An additional advantage of the use of the nonionic biodegradable ethoxylated alcohol surfactants according to the invention, is the absence of fluorescent background obtained when employing such surfactants as dye carrier in the dye penetrant, the Tergitol 15-S-9 being particularly effective in this respect.

The following examples serve to illustrate but are not limitative of the benefits and advantages obtained by practice of the present invention.

EXAMPLE 1

The fluorescent dye penetrant Composition II above was applied as by spraying, to one-half of the surface of a chromium-plated brass test panel containing minute cracks of the order of 0.00002 to 0.0001 inch in width, closely distributed over its entire surface. A water wash was then applied as by an air-water spray over the coating of the dye penetrant Composition II on the test panel, causing instantaneous washing away of the dye penetrant on the surface of the panel without dislodging the dye penetrant from the surface cracks and thus entrapping the penetrant therein. It appeared that the above-noted Tergitol 15-S-5 base penetrant has a high affinity for the cracks and defects in the panel surface, substantially greater than conventional dye penetrants.

The other half of the test panel surface was sprayed with a prior art fluorescent dye penetrant solution containing volatile ketone solvent and a phenyl polyethylene glycol ether surfactant, and required emulsifiers for removal of excess dye penetrant from the panel surface.

Both halves of the test panel surface to which penetrant Composition II above and the prior art dye penetrant were initially respectively applied, were then covered with a powder developer having the following composition, according to my above copending application Ser. No. 212,799.

| COMPONENTS | Per cent by weight |
|---|---|
| Talc | 52 |
| Alumina | 35 |
| Silica | 4 |
| TiO$_2$ | 9 |

The above developer was permitted to dwell over the two half surfaces of the test panel for a period of about 2 minutes.

Excess developer composition was then carefully removed from both half surfaces of the test panel by means of a gentle air blast.

The panel was then placed under black light (fluorescent) illumination and the respective half surfaces viewed in such illumination. It was observed that the first half side of the panel which had initially been treated with dye penetrant Composition II of the invention, disclosed fluorescent indications from numerous readily defined microcracks therein, such fluorescent indications being substantially brighter and revealing a greater concentration of the microcracks than the fluorescent indications from the microcracks on the half side of the panel which has been initially treated with the prior art dye penetrant.

EXAMPLE 2

Dye penetrant inspection tests were carried out in a manner generally similar to the procedure of Example 1, employing Composition III on a test panel containing cracks of intermediate size, and employing Composition IV on a test panel having gross cracks.

In each of the two tests above, bright fluorescent indications were obtained from the cracks of intermediate size on the first panel, and from the gross cracks on the second panel, employing Compositions III and IV, respectively, comparable to the brigtness and sensitivity of the fluorescent indications obtained employing composition II in Example 1. From Examples 1 and 2 above, it was observed that Composition II functions as a high sensitivity dye penetrant formulation for detecting microcracks, dye penetrant Composition III functions as a medium sensitivity dye penetrant for detecting intermediate size cracks, and dye penetrant Composition IV functions as a low sensitivity dye penetrant for detecting gross cracks. Thus there is provided according to the invention a dye penetrant composition having excellent sensitivity and which can be tailored for a large sensitivity range necessary to detect from the most minute microcrack to the largest gross crack, without requiring any change in the washability of the formulation. In other words, Compositions II, III and IV above all have the same washability characteristics when adequate amounts of water are used for washing, despite the differences in dye concentration of these respective compositions, such characteristics being unique and unexpected. Thus, it is believed that the dye penetrant of the invention employing the above defined ethoxylated alcohol surfactant carrier has the unique property of great affinity for remaining within the cracks and defects of a part, while that portion of the dye penetrant contacting the surface of the parts containing the cracks, can be instantaneously washed away with simple water spraying using adequate amounts of water, without dislodging the penetrant entrapments.

However, when the amount of wash water used is reduced, Composition II containing a larger amount of dye than Composition III was less readily washable, that is, was washed away at a slower rate, than Composition III, and Composition III containing a larger amount of dye than Composition IV, was less readily washable than Composition IV.

EXAMPLE 3

Tests on aluminum panels having a very smooth surface and containing microcracks of the order of 0.00002 to 0.0001 inch in width, were carried out employing procedure similar to that employed in Example 1, utilizing Composition I containing a combination of Tergitol 15-S-5 and Tergitol 15-S-3.

Results obtained were similar to those obtained in Example 1, but the test panel to which Composition I was applied required a more rigorous water wash than in the case of the test panel containing Composition II in Example 1.

EXAMPLE 4

The following dye penetrant compositions are also illustrative of the dye penetrant solutions of the invention;

Table 3

| COMPONENTS | Parts by weight | | | | |
|---|---|---|---|---|---|
| | II | III | IV | V | VI |
| Tergitol 15-S-5, 7, 9 or 12 | 90 | 88 | 92 | 95 | 94 |
| Calcofluor White | 6 | 8 | — | — | 4 |
| Fluorol 7GA | 4 | 4 | 8 | 5 | 2 |

EXAMPLE 5

The procedure of Example 1 was essentially followed, but employing in place of Composition II, a non-fluorescent water washable biodegradable dye penetrant solution according to the invention, consisting of 15 parts of Tergitol 15-S-5 and 1 part of Oil Red "0" dye, by volume, and employing a conventional non-fluorescent dye penetrant containing solvent and surfactant of the types noted in Example 1.

Excellent results of crack detectability were obtained employing such biodegradable non-fluorescent dye penetrant, as compared to the non-fluorescent prior art dye penetrant.

However, the brightness and sensitivity of the colored dye traces obtained employing the biodegradable non-fluorescent dye penetrant of this example were not as great as for the fluorescent biodegradable dye penetrant Composition II.

EXAMPLE 6

The procedure of Example 1 was followed except that in place of the powder developer employed in Example 1, a nonaqueous developer having the following composition, according to my above U.S. Pat. No. 3,748,469 was employed:

| COMPONENTS | Per Cent By Weight |
|---|---|
| Isopropyl alcohol | 70.5 |
| Talc | 28.6 |
| Glycol monobutyl ether | 0.9 |

The above developer was permitted to remain on the panel surfaces to which it was applied for a period of 2 minutes, until substantially all of the isopropyl alcohol had evaporated and a substantially dry powder coating was formed.

Results similar to the results of Example 1 were obtained.

From the foregoing, it is seen that the invention provides a highly effective substantially biodegradable water washable dye penetrant composition employing substantially a single carrier in the form of certain ethoxylated alcohols, which permits substantially instantaneous removal of dye penetrant from the surface of the part in a single wash operation, while maintaining the dye penetrant in the cracks or defects of the part, followed by further processing of the dye penetrant coating as desired in the conventional manner for viewing under suitable e.g. fluorescent, lighting conditions, to obtain improved brilliance, definition and resolution of dye traces from cracks and flaws in the part surface, as compared to prior art penetrants, and affording a substantially non-flammable high performance dye penetrant composition having a wide range of sensitivity, which results in a surface substantially free of undesirable fluorescent background, especially in rough metallic surfaces, and avoiding the use of volatile extenders and thinners in the dye penetrant.

Since various changes and modifications of the invention will occur to and can be made readily by those skilled in the art without departing from the invention concept, the invention is not to be taken as limited except by the scope of the appended claims.

I claim:

1. A method for detecting cracks and flaws in the surface of an object, which comprises applying to said surface a water washable biodegradable liquid dye penetrant composition which consists essentially of (1) a major amount of a liquid nonionic surfactant in the form of ethoxylates of a mixture of linear secondary aliphatic alcohols, with the hydroxyl groups randomly distributed, the linear aliphatic portion of said alcohols being a mixture of alkyl chains containing in the range from 10 to 17 carbon atoms, and containing an average of from 3 to 12 moles of ethylene oxide; and (2) a small amount of a dye soluble in said surfactant, removing said dye penetrant composition from said surface without removing said dye penetrant composition from said cracks and flaws in said surface, and viewing the surface of said object under lighting conditions to obtain colored traces from the dye in said cracks and flaws.

2. A method as defined in claim 1, wherein said liquid dye penetrant composition consists, essentially of said nonionic surfactant as the sole liquid carrier for said dye and the mixture of alkyl chains contains in the range from 11 to 15 carbon atoms.

3. A method as defined in claim 1, said removal of said dye penetrant composition being carried out by application of a water wash over said surface.

4. A method as defined in claim 3, said water wash being carried out by spraying water over said surface.

5. A method as defined in claim 1, wherein said dye is a fluorescent dye and said surface of said object is viewed under fluorescigenous light to obtain colored fluorescent traces from the dye in said cracks and flaws.

6. A method as defined in claim 1, including applying a developer to said surface after removing said dye penetrant composition from said surface and prior to said viewing the surface of said object.

7. A method as defined in claim 1, wherein said ethoxylates of said mixture of alcohols forming said surfactant have the formula:

$$CH_3-(CH_2)_n-CH_3$$
$$|$$
$$O-(CH_2-CH_2O)_m-H$$

where n is in the range 9 to 13 and m is 3 to 12, and said dye is present in said composition in an amount ranging from about 0.1 to 15 parts per 100 parts, by weight, of said surfactant.

8. A method as defined in claim 7, wherein the linear alkyl hydrophobic portion of said surfactant is a mixture of $C_{11}$ to $C_{15}$ linear chains, the hydrophilic portion of said surfactant is a polyoxyethylene chain randomly attached to the linear alkyl hydrophobic chains through an ether linkage, said dye is present in said composition in an amount ranging from about 0.1 to 15 parts, per 100 parts, by weight, of said surfactant, and the mixture of alkyl chains contains in the range from 11 to 15 carbon atoms.

9. A method as defined in claim 8, wherein said surfactant is selected from the group consisting of said ethoxylates of said mixture of alcohols, wherein n ranges from 9 to 13, and m is an average of 3, 5, 7, 9 and 12, respectively.

10. A method as defined in claim 7, wherein said dye is a fluorescent dye and said surface of said object is viewed under fluorescigenous light to obtain colored fluorescent traces from the dye in said cracks and flaws.

11. A method as defined in claim 9, wherein said dye is a fluorescent dye and said surface of said object is viewed under fluorescigenous light to obtain colored fluorescent traces from the dye in said cracks and flaws.

12. A method as defined in claim 11, said removal of said dye penetrant composition being carried out by application of a water wash over said surface.

13. A method as defined in claim 12, said dye penetrant compositions containing larger amounts of said dye being less readily washable by said water wash than said dye penetrant composition containing smaller amounts of said dye.

14. A method as defined in claim 11, said removal of said dye penetrant composition being carried out by wiping said surface with a water moistened cloth.

15. A method as defined in claim 11, said removal of said dye penetrant composition being carried out by wiping said surface with a cloth moistened with a rapid drying solvent.

16. A method as defined in claim 9, wherein said surfactant is a combination of said ethoxylates.

17. A method as defined in claim 9, wherein said surfactant is a combination of said ethoxylates where m is 3 and where m is 5.

18. A method as defined in claim 9, wherein said surfactant is a combination of said ethoxylates where m is 3 and where m is 9.

* * * * *